US011298491B1

(12) United States Patent
Anand et al.

(10) Patent No.: US 11,298,491 B1
(45) Date of Patent: Apr. 12, 2022

(54) SYSTEM, DEVICE, AND ARRANGEMENT FOR A MANUAL VENTILATION ASSISTANT

(71) Applicant: Accenture Global Solutions Limited, Dublin (IE)

(72) Inventors: Narendra Anand, Houston, TX (US); Sarah Crabb, Houston, TX (US); Arnob Bhuyan, The Woodlands, TX (US)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 16/949,551

(22) Filed: Nov. 3, 2020

(51) Int. Cl.
| | | |
|---|---|---|
| A61M 16/00 | (2006.01) | |
| A61M 16/06 | (2006.01) | |
| A61M 16/20 | (2006.01) | |

(52) U.S. Cl.
CPC ........ *A61M 16/06* (2013.01); *A61M 16/0003* (2014.02); *A61M 16/20* (2013.01); *A61M 2016/003* (2013.01); *A61M 2016/0027* (2013.01); *A61M 2205/50* (2013.01); *A61M 2205/75* (2013.01)

(58) Field of Classification Search
CPC .......... A61M 16/0078; A61M 16/0084; A61M 2016/0027; A61M 2205/581; A61M 2205/583; A61M 2016/0036; A61M 16/00; A61M 16/0858
See application file for complete search history.

(56) References Cited

U.S. PATENT DOCUMENTS

| | | | | |
|---|---|---|---|---|
| 5,347,843 | A * | 9/1994 | Orr | G01F 1/363 600/538 |
| 2012/0302910 | A1 * | 11/2012 | Freeman | A61M 16/0084 600/538 |
| 2015/0107584 | A1 * | 4/2015 | Jafari | A61M 16/0063 128/202.22 |
| 2015/0283342 | A1 | 10/2015 | Mielcarz et al. | |
| 2016/0374592 | A1 * | 12/2016 | Lee | A61B 5/097 600/532 |
| 2017/0266399 | A1 * | 9/2017 | Campana | A61M 16/107 |

(Continued)

OTHER PUBLICATIONS

Tipparaju et al., "Reliable Breathing Tracking With Wearable Mask Device," IEEE Sensors Journal, vol. 20, No. 10, May 15, 2020, pp. 5510-5518.

(Continued)

*Primary Examiner* — Margaret M Luarca
(74) *Attorney, Agent, or Firm* — Harrity & Harrity, LLP

(57) ABSTRACT

In some implementations, a system may receive, from a differential pressure sensor, a differential pressure measurement associated with a differential pressure across an air filter within an airway of a manual ventilator. The system may determine, based on the differential pressure measurement, an air flow rate through the airway. The system may determine timing of a compression cycle of the manual ventilator. The system may determine, based on the timing, a flow threshold associated with a desired breathing cycle. The system may determine a difference between the flow threshold and the air flow rate. The system may provide, via a display associated with the manual ventilator, a representation associated with the difference to indicate whether a compression parameter of the compression cycle is to be adjusted.

20 Claims, 3 Drawing Sheets

(56) References Cited

U.S. PATENT DOCUMENTS

2020/0061319 A1 2/2020 Hansmann et al.
2020/0222647 A1* 7/2020 Marascalchi .......... A61B 5/087

OTHER PUBLICATIONS

Shaikh et al., "Respiratory Parameter Measurement and Analysis using Differential Pressure Sensor," International Conference on Communication and Signal Processing, Apr. 6-8, 2017, India, 4 Pages.

* cited by examiner

SYSTEM, DEVICE, AND ARRANGEMENT FOR A MANUAL VENTILATION ASSISTANT

BACKGROUND

A ventilator is a mechanism that provides mechanical ventilation by moving breathable air into and out of lungs of an individual (e.g., a patient) to facilitate breathing for the individual, who may be physically unable to breathe and/or unable to sufficiently breathe. In some cases, a ventilator includes a machine with an automatically controlled and/or electronically controlled compression system (e.g., a system that includes an air compressor) to supply the breathable air. In other cases, a ventilator (e.g., a manual resuscitator; a bag, valve, mask (BVM), or the like) includes a manually controlled compression mechanism (e.g., a self-inflating bag) that is to be compressed (and/or squeezed) by a user (e.g., a first responder, doctor, nurse, or the like) to supply the breathable air.

SUMMARY

In some implementations, a method includes receiving, from a differential pressure sensor, a differential pressure measurement associated with a differential pressure across an air filter within an airway of a manual ventilator; determining, based on the differential pressure measurement, an air flow rate through the airway; determining timing of a compression cycle of the manual ventilator; determining, by the device and based on the timing, a flow threshold associated with a desired breathing cycle; determining a difference between the flow threshold and the air flow rate; and providing, via a display associated with the manual ventilator, a representation associated with the difference to indicate whether a compression parameter of the compression cycle is to be adjusted.

In some implementations, a device includes one or more memories and one or more processors, communicatively coupled to the one or more memories, configured to: receive a differential pressure measurement associated with a differential pressure across an air filter within an airway of a manual ventilator; determine, based on the differential pressure measurement, an air flow rate through the airway; determine, based on the air flow rate and a flow threshold, whether a compression parameter of the manual ventilator requires adjustment; and provide, via a display associated with the manual ventilator, an indication associated with whether the compression parameter requires adjustment.

In some implementations, a manual ventilation system may include: a manual ventilator; a coupling configured to be fluidly coupled to the manual ventilator, wherein the coupling includes an air filter; a differential pressure sensor configured to measure a differential pressure across the air filter via a first sensor line and a second sensor line; a patient-side opening configured to fluidly couple a ventilator airway of the manual ventilator with a patient airway; and a ventilation monitor configured to: receive a differential pressure measurement from the differential pressure sensor; determine, based on the differential pressure measurement, an air flow rate through the ventilator airway; and provide, via a display associated with the manual ventilator, an indication associated with the air flow rate.

DETAILED DESCRIPTION

Figure 1:
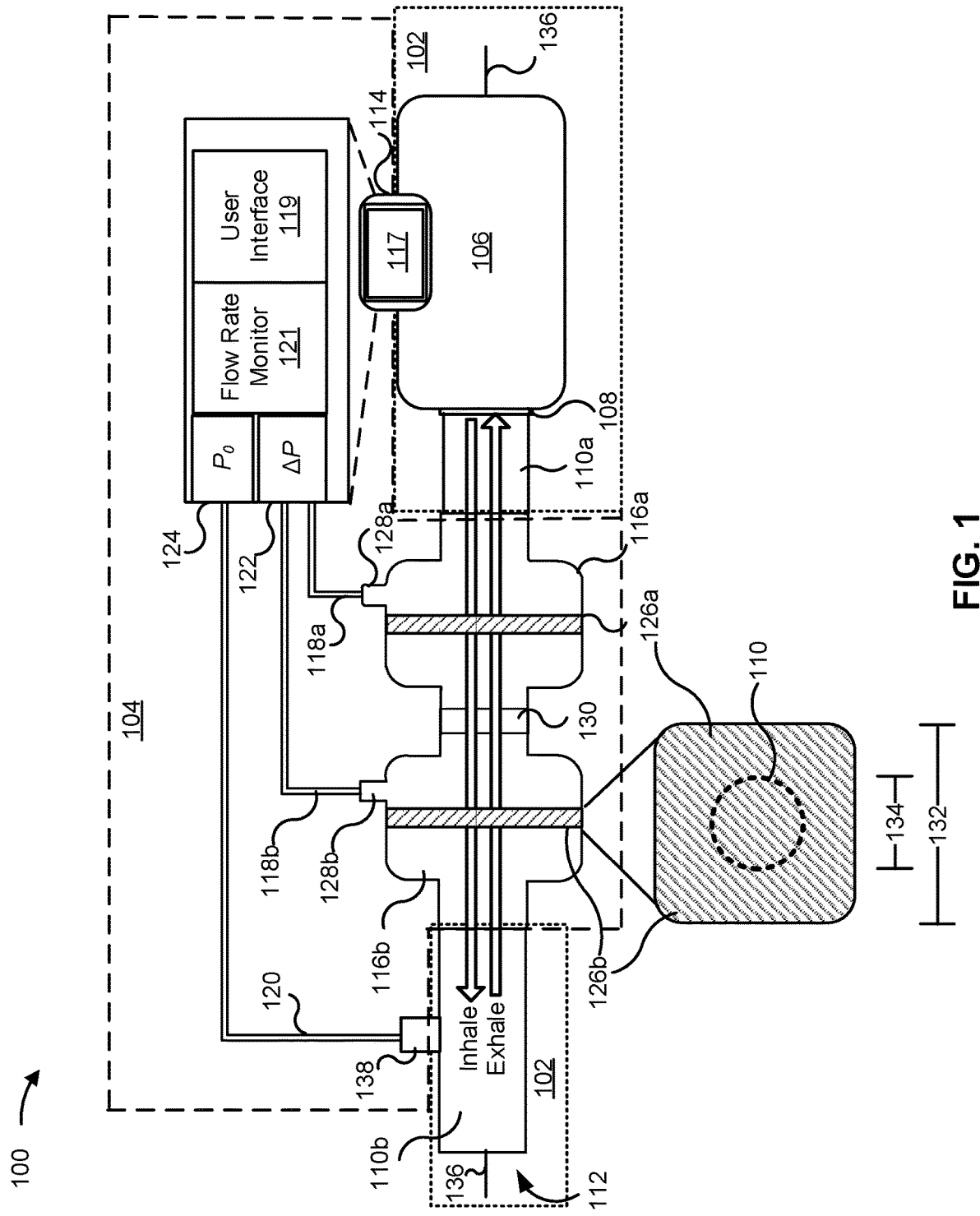
FIG. 1 is a diagram of an example implementation of a manual ventilation system described herein.

The following detailed description of example implementations refers to the accompanying drawings. The same reference numbers in different drawings may identify the same or similar elements.

Ventilation systems (which may be referred to as "ventilators," "resuscitators," among other examples) are crucial medical devices that are frequently used to save lives in emergencies, during certain health related episodes, or the like. Machine-based (or automated) ventilators are typically owned and/or operated in certain healthcare facilities (e.g., hospitals, doctor offices, and/or the like), and thus are not readily available to a patient in need (e.g., a patient that is remotely located from such a healthcare facility) and/or may not be accessible to a patient that is not at such a healthcare facility (e.g., in the event of a health-related emergency or accident) (e.g., due to the physical size and/or weight of the ventilator and/or due to the ventilator requiring a power source). Furthermore, during a relatively widespread crisis (e.g., an epidemic, a pandemic, or the like), these healthcare facilities may have limited access to machine-based ventilators due to the increased demand caused by the widespread crisis. Such limited access may prevent a patient from being able to use a machine-based ventilator in a timely manner, resulting in potentially catastrophic results (e. g., brain damage, death, and/or the like).

While manual ventilators are more widely available than machine-based ventilators (e.g., due to requiring less complex hardware, not requiring a power source to power a motorized compression mechanism, or the like), the effectiveness of manual ventilators is subject to the expertise and/or experience of the users using the manual ventilators to control breathing for patients. For example, a user (e.g., a first responder, a bystander, a doctor, a nurse, or the like) may ineffectively use a manual ventilator by compressing the manual compression mechanism improperly (e.g., too quickly, too slowly, too frequently, not frequently enough, or the like), such that a patient is not receiving an appropriate amount of air to breathe (and/or supply oxygen to vital organs of the patient). Moreover, although manual ventilators are more widely available, certain components of the manual ventilators need to be decontaminated (and/or sanitized) between uses with different patients to prevent the spread of diseases between the patients.

According to some implementations described herein, a manual ventilator assistant is provided and is configured to operate in association with a manual ventilator to assist a user of the ventilator with properly supplying air to a patient during use. For example, as described herein, the manual ventilator assistant may include one or more pressure sensors to measure air flow through the manual ventilator, a flow rate monitor to analyze measurements of the air flow relative to a flow threshold, and a user interface to indicate whether the user should adjust a parameter of a compression cycle (e.g., a compression rate, a frequency of compressions, or the like). In some implementations, the manual ventilator assistant may include one or more air filters (e.g., filters configured to absorb and/or prevent passage of particles through the air filters) within detachable couplings (e.g., disposable couplings, replaceable couplings, or the like) to prevent one or more components (e.g., sensors, displays, speakers, or the like) and/or one or more instruments (e.g., flow lines, valves, couplings, or the like) of the manual ventilator assistant from being contaminated. In this way, the manual ventilator assistant may be configured for reuse with different patients while preventing the one or more components from harboring germs, viruses, or bacteria, which can be spread to another patient without the manual ventilator assistant being properly decontaminated at a sanitation facility, which may not be readily available between uses of the manual ventilator assistant.

Furthermore, the manual ventilator assistant and/or manual ventilator, as described herein, can increase the availability of effective ventilators based on being formed from more readily available parts relative to a machine-based ventilator, which requires a motorized compressor, a power source for the motorized compressor, or the like. Moreover, the manual ventilator assistant and/or manual ventilator described herein consumes fewer hardware resources (e.g., than a motorized compressor), consumes less power (e.g., without having to supply power to a motorized compressor), and is less cumbersome (e.g., lighter in weight, smaller in size, or the like) than machine-based ventilators, while improving effectiveness of manual ventilators (e.g., by permitting users to more accurately monitor breathing and/or facilitate breathing for a patient, relative to not using the manual ventilator assistant as performed in previous techniques).

FIG. 1 is a diagram of an example manual ventilation system 100 associated with a manual ventilator assistant. As shown in FIG. 1, the manual ventilation system 100 includes a manual ventilator 102 (outlined with dotted lines) and a manual ventilator assistant 104 (outlined with dashed lines).

The manual ventilator 102 includes a manual compression mechanism 106, a valve 108, one or more flow lines 110 (shown as and referred to herein individually as the "flow line 110a" and "flow line 110b," and collectively as the "flow lines 110"), and a patient-side opening 112. The manual compression mechanism 106, valve 108, and patient-side opening 112 may correspond to and/or be associated with a BVM. For example, the manual compression mechanism 106 may include a self-inflating bag of the BVM, the valve 108 may correspond to a unidirectional and/or multi-directional valve system of a BVM, and the patient-side opening 112 may correspond to a mask or other type of fitting mechanism configured to fluidly couple the flow line 110 to an airway of a patient (referred to herein as a "patient airway"). In some implementations, the manual ventilator 102 is a preconfigured assembly, a preconfigured kit, or the like that is capable of being fit with the manual ventilator assistant 104, as described herein.

The manual ventilator assistant 104 includes a ventilation monitor 114, one or more couplings 116 (shown as and referred to herein individually as "coupling 116a" or "coupling 116b," and collectively as "couplings 116"), one or more differential pressure sensor lines 118 (shown as and referred to herein individually as "differential pressure sensor line 118a" or "differential pressure sensor line 118b," and collectively as "differential pressure sensor lines 118"), and an absolute pressure sensor line 120. The ventilation monitor 114 includes a display 117, a user interface 119, a flow rate monitor 121, a differential pressure (ΔP) sensor 122, and an absolute pressure ($P_O$) sensor 124.

The couplings 116 include one or more air filters 126 (shown as and referred to herein as "air filter 126a" or "air filter 126b," and collectively as "air filters 126") and differential pressure sensor line connectors 128 (shown as and referred to herein as "differential pressure sensor line connector 128a" or "differential pressure sensor line connector 128b," and collectively as "differential pressure sensor line connectors 128"). The couplings 116 may be fluidly coupled to each other via a coupler 130. In some implementations, the couplings 116 may be a single coupling (e.g., a single coupling that includes two or more air filters 126, as described herein).

As described herein, an airway (shown by an "Inhale" arrow and an "Exhale" arrow) of the manual ventilator 102 (which may be referred to herein as a "ventilator airway") corresponds to an air passage formed by the manual compression mechanism 106, the valve 108, the flow lines 110, and the couplings 116. Accordingly, the air filters 126 of the example manual ventilation system 100 are positioned within the airway of the manual ventilator 102. The air filters 126 may be certified (e.g., according to a manufacturing standard) to absorb and/or block 95% of airborne particles (e.g., as an N95 filter), 99% of airborne particles (e.g., as an N99 filter), or the like. As shown in FIG. 1, a cross-sectional area 132 of the couplings 116 and/or the air filters 126 is greater than a cross-sectional area 134 of the airway. The cross-sectional area 134 may correspond to an average cross-sectional airway, a narrowest cross-sectional area of the airway, a cross-sectional area of the flow lines 110, a cross-sectional area of the patient-side opening 112, a cross-sectional area of an outlet of the valve 108, or the like. The cross-sectional area 132 and the cross-sectional area 134 may be within planes that are perpendicular to a direction of airflow of the airway, a central axis 136 of the airway, or the like.

The flow rate monitor 121 is configured to determine an air flow rate based on a differential pressure measurement (ΔP) from the differential pressure sensor 122. As described herein, the differential pressure sensor 122 is fluidly coupled to the airway via the differential pressure sensor lines 118 and the differential pressure sensor line connectors 128. In the example of FIG. 1, the air filter 126a affects air flow through the coupling 116a. Additionally, or alternatively, the difference between the cross-sectional area 132 of the couplings 116 and/or air filters 126 and the cross-sectional area 134 may affect the air flow through the coupling 116a.

In this way, the differential pressure sensor 122 may sense a difference in pressure across the air filter 126a. For example, as shown, the differential pressure sensor 122 is configured to obtain a first pressure measurement via differential pressure sensor line 118a and a second pressure measurement via the different pressure sensor line 118b. Accordingly, the differential pressure sensor 122 may determine and/or provide a differential pressure sensor measurement that corresponds to a difference in the first and second pressure measurement. The differential pressure sensor measurement may include a polarity relative to whether the first pressure measurement is greater than the second pressure measurement, or vice versa. Accordingly, the flow rate monitor 121, based on the polarity of the differential pressure measurement across the air filter 126a, may determine a direction of the air flow and/or an air flow rate through the airway. For example, if the polarity of the differential pressure measurement indicates that the first pressure measurement is greater than the second pressure measurement, the flow rate monitor 121 may correspondingly determine that the manual compression mechanism 106 is being compressed by the user. Additionally, or alternatively, if the polarity of the differential pressure measurement indicates that the second pressure measurement is greater than the first pressure measurement, the flow rate monitor 121 may correspondingly determine that the patient is exhaling and/or that the manual compression mechanism 106 is inflating.

The absolute pressure sensor 124 is fluidly coupled to the airway via absolute pressure line 120 and an absolute pressure sensor line connector 138 of the flow line 110b. Accordingly, the absolute pressure sensor 124 may determine an air pressure by obtaining an absolute pressure measurement ($P_O$) of the airway near or toward the patient-side opening 112 (e.g., a patient-side of the air filters 126). Such an air pressure may correspond to an inspiratory air pressure of the patient-side opening 112 (e.g., indicating an amount of air being inhaled by a patient). In some implementations, an air filter (e.g., similar to the air filters 126) may be positioned within the absolute pressure sensor line 120 and/or the absolute pressure sensor line connector 138. Such an air filter may prevent unfiltered (or non-sanitary) air in the flow line 110b from reaching the absolute pressure line 120 and/or the absolute pressure sensor 124.

According to some implementations, the flow rate monitor 121 may determine an air flow rate through the airway based on the following:

$$Q = C_f A_O \sqrt{\frac{2\Delta P}{P_O}} \quad (1)$$

where Q is the air flow rate, $A_O$ is the cross-sectional area 134, $P_O$ is the absolute pressure measurement, $\Delta P$ is the differential pressure measurement, and $C_f$ is a constant that may be used to calibrate the flow rate monitor 121. According to some implementations, $C_f$ may be set or calibrated according to one or more characteristics of the couplings 116 (e.g., type, size (such as cross-sectional area), and/or the like) and/or the air filters 126 (e.g., type, size, filter rating, or the like). In some implementations, $C_f$ may be set and/or defined based on a determined accuracy level of the differential pressure sensor 122 and/or the absolute pressure sensor 124, based on the cross-sectional area 132 of the couplings 116 and/or the air filters 126, or the like. In some implementations, the flow rate monitor 121 may receive $A_O$ and/or $C_f$ via a user input received via the user interface 119. For example, the user input may specify and/or identify the cross-sectional 134 area of the airway to permit the flow rate monitor 121 to determine the air flow rate based on the differential pressure measurement and/or the absolute pressure measurement.

In some implementations, $C_f$ may be adjustable and/or configurable (e.g., as an output of a function) based on one or more individual characteristics of a patient that is to receive a breathing treatment via the manual ventilation system 100. Such individual characteristics may include an age of the patient, a height of the patient, a weight of the patient, a health condition of the patient (e.g., whether the user is known to have a particular injury or disease), and/or any other individual characteristic that might affect the patient's ability to breathe. In this way, the flow rate monitor 121 may determine an air flow rate through the airway based on a different pressure measurement (e.g., across the air filter 126a), an absolute pressure measurement (e.g., near or toward the patient-side opening 112), a cross-sectional area (e.g., the cross-sectional area 132 and/or the cross-sectional area 134) of the airway, and/or the like.

According to some implementations, the flow rate monitor 121 may determine a desired breathing cycle for a patient being treated by the manual ventilation system 100. For example, the flow rate monitor 121 may determine the desired breathing cycle based on the above individual characteristics of the patient, one or more characteristics of the manual ventilation system 100, and/or a configuration or arrangement of the manual ventilation system 100 (e.g., corresponding to relative positioning of the components of the manual ventilator 102 and/or the manual ventilator assistant 104), or the like. The desired breathing cycle may define timing, flow levels, and/or directions of breaths of the patient. For example, one desired cycle may include a duration of an inhalation, an air flow rate of the inhalation (e.g., at various moments of the inhalation), a duration of an exhalation, and an air flow rate of the exhalation (e.g., at various moments of the exhalation).

The desired breathing cycle may be associated with and/or define a flow threshold for the air flow rate through the airway. For example, the flow rate monitor 121 may compare the air flow rate with an air flow rate of the desired breathing cycle to determine whether a compression parameter of the manual compression mechanism 106 is to be adjusted (e.g., increased or decreased). More specifically, at a given moment of the flow rate monitor 121 receiving the differential pressure measurement and/or the absolute pressure measurement, based on a direction of the air flow through the airway (e.g., as determined by the polarity of the differential pressure measurement) and a timestamp of initiating a most recent compression, the flow rate monitor 121 may determine timing of a breathing cycle of the patient (which may be referred to herein as a "patient breathing cycle"). Based on the timing of the patient breathing cycle, the flow rate monitor 121 may determine a flow threshold as a flow level at a corresponding time of the desired breathing cycle.

Additionally, or alternatively, the flow rate monitor 121 may compare the air flow rate with the determined flow threshold to determine whether a compression parameter of the manual compression mechanism 106 (and/or a compression cycle of the manual compression mechanism 106) requires an adjustment. The flow rate monitor 121 may determine that an adjustment is required when a difference between the air flow rate and the flow threshold satisfies a difference threshold. For example, the flow rate monitor 121 may determine that a compression rate is to be increased when the air flow rate is below the flow threshold for the air flow by a difference threshold and/or by more than the difference threshold (e.g., a percentage, such as 70%, 80%, or the like of a corresponding flow level of the desired breathing cycle). Alternatively, the flow rate monitor 121 may determine that the compression rate is to be decreased when the air flow rate is above the flow threshold by the difference threshold or more than the difference threshold (e.g., a percentage, such as 110%, 130%, or the like of the corresponding flow level of the desired breathing cycle). In this way, the ventilation monitor 114 (e.g., via the flow rate monitor 121) may determine that a compression parameter requires an adjustment based on whether a difference between the flow threshold and the air flow rate satisfies a difference threshold.

As described herein, the air filters 126 are configured to absorb and/or prevent airborne particles within the airway from reaching the differential pressure sensor lines 118. For example, as shown, the differential pressure sensor lines 118 are fluidly coupled to the couplings via the differential pressure sensor line connectors 128. More specifically, the differential pressure sensor line 118a is fluidly coupled to the airway (e.g., via the differential pressure sensor line connector 128a) toward a manual compression mechanism 106 side of the air filter 126a, and the differential pressure sensor line 118*b* is fluidly coupled (e.g., via differential pressure sensor line connector 128*b*) to the airway between the air filters 126. Contaminated air may be exhaled by the patient through the patient-side opening 112. Accordingly, unfiltered air may be within the flow line 110*b*. However, the air filter 126*b* prevents the contaminated air from reaching the differential pressure sensor lines 118. Furthermore, contaminated ambient air may be supplied into the flow line 110*a* during a compression of the manual compression mechanism 106. However, the air filter 126*a* prevents the contaminated air in the flow line 110*a* from reaching the differential pressure sensor lines 118. In this way, the air filters 126 may ensure that air within the airway between the air filters 126 remains decontaminated during use with a patient, thereby ensuring that the differential pressure sensor lines 118 and/or the differential pressure sensor 122 remains decontaminated during or after use with the patient. Accordingly, following use with the patient, the differential pressure sensor lines 118 and/or the differential pressure sensor 122 can be reused with another patient without having to be decontaminated (e.g., at a sanitation facility).

The display 117 may be associated with the user interface 119 (e.g., as an output component of the user interface 119). While shown as connected or attached to the manual compression mechanism 106, the ventilation monitor 114 (and/or the display 117) may be arranged or configured in any suitable location that would be within view of a user compressing the manual compression mechanism 106. The user interface 119 may be associated with one or more user input components (e.g., a keyboard, buttons, a touchscreen, or the like) to permit a user to control and/or configure settings for the ventilation monitor 114. Additionally, or alternatively, the user interface may include one or more output components (e.g., the display 117, a speaker, a light emitter, or the like) to provide an indication to a user of the manual ventilation system 100 and/or to permit the manual ventilator assistant 104 to assist a user with using the manual ventilator 102 to control breathing of a patient. Accordingly, the ventilation monitor 114 may visually and/or audibly indicate whether a compression parameter of a compression cycle of the manual ventilator 102 requires an adjustment, in real-time, to permit the user to provide an optimal amount of air flow to the patient.

As described herein, the flow rate monitor 121 is configured to provide an indication to a user that is associated with whether an adjustment to a compression parameter of a compression cycle being performed by the user is required. For example, the compression parameter, at a given moment of a compression cycle, may correspond to a compression rate (e.g., a rate at which the user is compressing the manual compression mechanism 106), an amount of compression that is to be applied to the manual compression mechanism 106 (e.g., an acceleration of compressing the manual compression mechanism 106 and/or intensity of compressing the manual compression mechanism 106), a frequency of compressing the manual compression mechanism 106 (e.g., a period of time between compressions of the compression cycle) or the like. In this way, in real-time, and based on timing of a compression cycle of the manual ventilator 102 (e.g., a compression cycle of the user compressing the manual compression mechanism 106) and/or a measured breathing cycle of the patient (e.g., based on the determined air flow rate), the ventilation monitor 114 may indicate to the user whether the compression parameter requires an adjustment relative to the flow threshold associated with the compression cycle.

Accordingly, the manual ventilation system 100, being configured with the manual ventilator assistant 104, may permit a user to operate the manual ventilator 102 more effectively to treat a patient, thereby improving the probability of preventing harm to the patient, improving a breathing capability of the patient, and/or improving a probability that the patient survives a catastrophic event that required assistance from a ventilator. Moreover, the manual ventilator assistant 104 is configured to be reusable for multiple treatments of various patients by ensuring that components of the manual ventilator assistant 104 remain decontaminated across the multiple treatments by using replaceable (e.g., disposable and/or reusable) couplings and/or filters that are readily available and/or that may be preconfigured to fit within an airway of the manual ventilator 102. Correspondingly, the manual ventilator assistant 104, as arranged within the example manual ventilation system 100, can improve the availability of effective ventilation systems in areas and/or locations where access to machine-based ventilators is limited.

As indicated above, FIG. 1 is provided as an example. Other examples may differ from what is described with regard to FIG. 1. The number and arrangement of devices shown in FIG. 1 are provided as an example. In practice, there may be additional devices, fewer devices, different devices, or differently arranged devices than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) shown in FIG. 1 may perform one or more functions described as being performed by another set of devices shown in FIG. 1.

Figure 2:
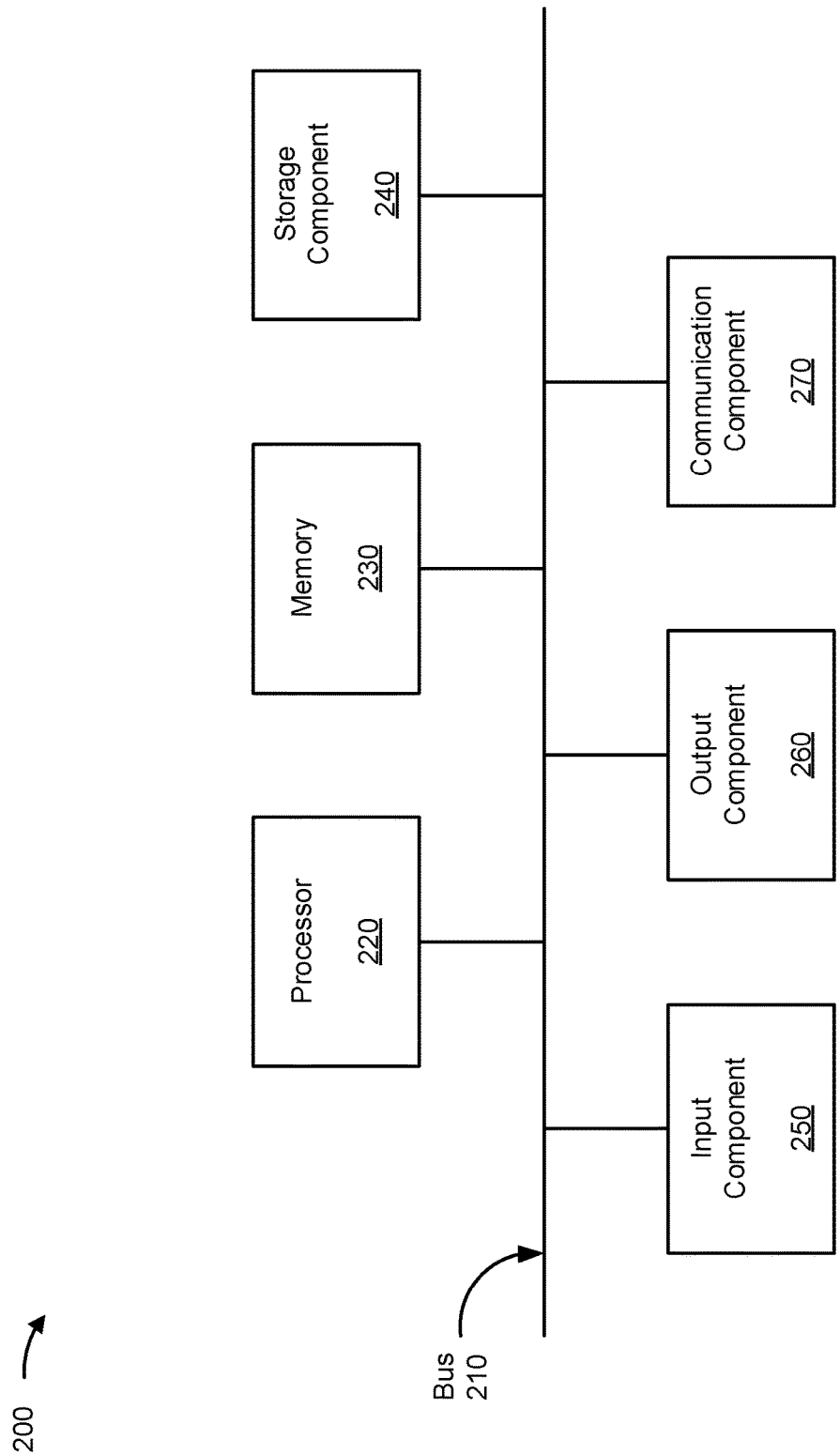
FIG. 2 is a diagram of example components of one or more devices of FIG. 1.

FIG. 2 is a diagram of example components of a device 200, which may correspond to the ventilation monitor 114 of FIG. 1. In some implementations, the ventilation monitor 114 may include one or more devices 200 and/or one or more components of device 200. As shown in FIG. 2, device 200 may include a bus 210, a processor 220, a memory 230, a storage component 240, an input component 250, an output component 260, and a communication component 270.

Bus 210 includes a component that enables wired and/or wireless communication among the components of device 200. Processor 220 includes a central processing unit, a graphics processing unit, a microprocessor, a controller, a microcontroller, a digital signal processor, a field-programmable gate array, an application-specific integrated circuit, and/or another type of processing component. Processor 220 is implemented in hardware, firmware, or a combination of hardware and software. In some implementations, processor 220 includes one or more processors capable of being programmed to perform a function. Memory 230 includes a random access memory, a read only memory, and/or another type of memory (e.g., a flash memory, a magnetic memory, and/or an optical memory).

Storage component 240 stores information and/or software related to the operation of device 200. For example, storage component 240 may include a hard disk drive, a magnetic disk drive, an optical disk drive, a solid state disk drive, a compact disc, a digital versatile disc, and/or another type of non-transitory computer-readable medium. Input component 250 enables device 200 to receive input, such as user input and/or sensed inputs. For example, input component 250 may include a touch screen, a keyboard, a keypad, a mouse, a button, a microphone, a switch, a sensor, a global positioning system component, an accelerometer, a gyroscope, and/or an actuator. Output component 260 enables device 200 to provide output, such as via a display, a speaker, and/or one or more light-emitting diodes. Communication component 270 enables device 200 to communicate with other devices, such as via a wired connection and/or a wireless connection. For example, communication component 270 may include a receiver, a transmitter, a transceiver, a modem, a network interface card, and/or an antenna.

Device 200 may perform one or more processes described herein. For example, a non-transitory computer-readable medium (e.g., memory 230 and/or storage component 240) may store a set of instructions (e.g., one or more instructions, code, software code, and/or program code) for execution by processor 220. Processor 220 may execute the set of instructions to perform one or more processes described herein. In some implementations, execution of the set of instructions, by one or more processors 220, causes the one or more processors 220 and/or the device 200 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 2 are provided as an example. Device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
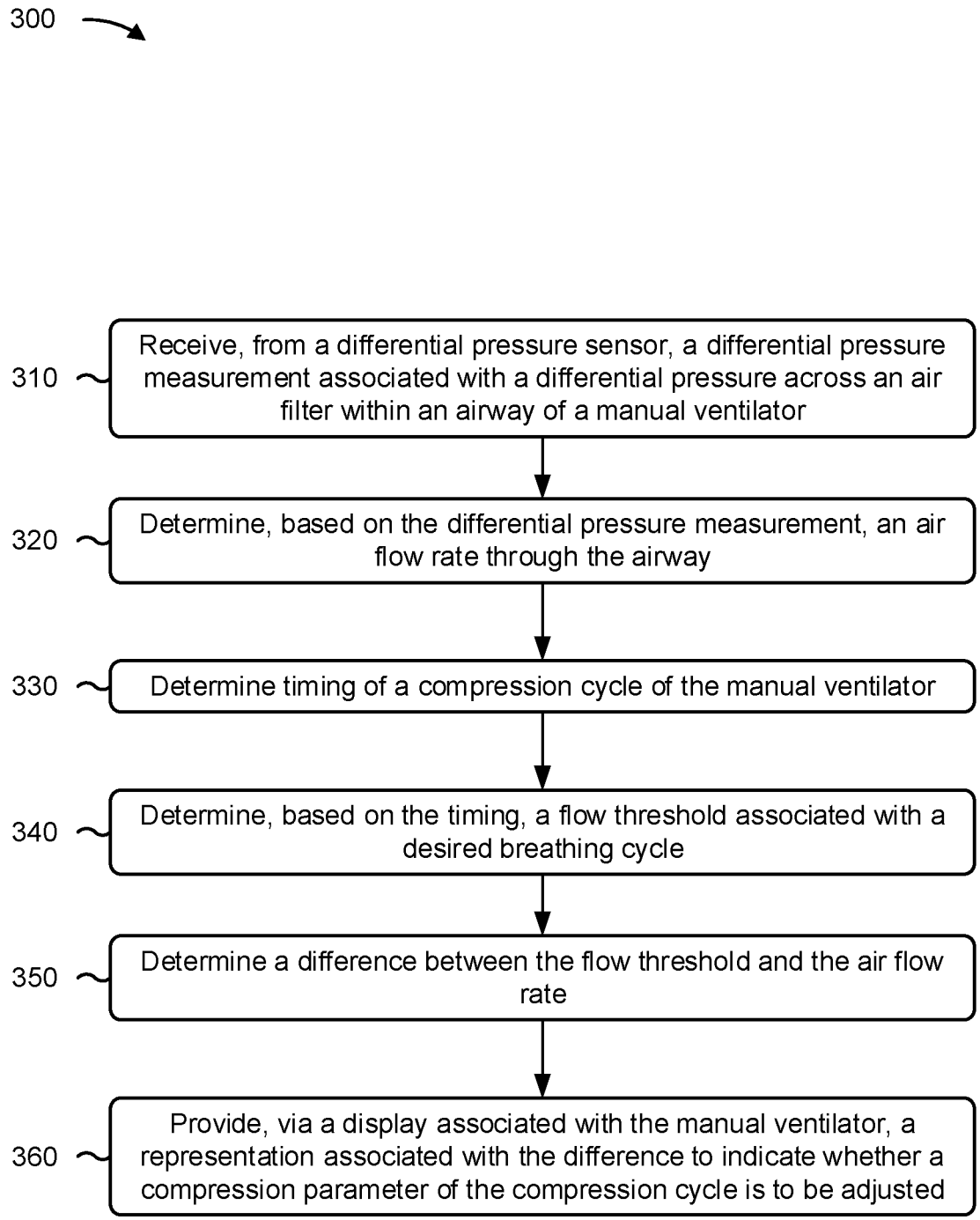
FIG. 3 is a flowchart of an example process relating to a manual ventilator assistant.

FIG. 3 is a flowchart of an example process 300 associated with a system, device, and arrangement for a manual. In some implementations, one or more process blocks of FIG. 3 may be performed by a ventilation monitor (e.g., ventilation monitor 114). Additionally, or alternatively, one or more process blocks of FIG. 3 may be performed by one or more components of device 200, such as processor 220, memory 230, storage component 240, input component 250, output component 260, and/or communication component 270.

As shown in FIG. 3, process 300 may include receiving, from a differential pressure sensor, a differential pressure measurement associated with a differential pressure across an air filter within an airway of a manual ventilator (block 310). For example, the ventilation monitor may receive, from a differential pressure sensor, a differential pressure measurement associated with a differential pressure across an air filter within an airway of a manual ventilator, as described above.

As further shown in FIG. 3, process 300 may include determining, based on the differential pressure measurement, an air flow rate through the airway (block 320). For example, the ventilation monitor may determine, based on the differential pressure measurement, an air flow rate through the airway, as described above.

As further shown in FIG. 3, process 300 may include determining timing of a compression cycle of the manual ventilator (block 330). For example, the ventilation monitor may determine timing of a compression cycle of the manual ventilator, as described above.

As further shown in FIG. 3, process 300 may include determining, based on the timing, a flow threshold associated with a desired breathing cycle (block 340). For example, the ventilation monitor may determine, based on the timing, a flow threshold associated with a desired breathing cycle, as described above.

As further shown in FIG. 3, process 300 may include determining a difference between the flow threshold and the air flow rate (block 350). For example, the ventilation monitor may determine a difference between the flow threshold and the air flow rate, as described above.

As further shown in FIG. 3, process 300 may include providing, via a display associated with the manual ventilator, a representation associated with the difference to indicate whether a compression parameter of the compression cycle is to be adjusted (block 360). For example, the ventilation monitor may provide, via a display associated with the manual ventilator, a representation associated with the difference to indicate whether a compression parameter of the compression cycle is to be adjusted, as described above.

Process 300 may include additional implementations, such as any single implementation or any combination of implementations described below and/or in connection with one or more other processes described elsewhere herein.

In a first implementation, a first sensor input of the differential pressure sensor is fluidly coupled to the airway toward a manual ventilator-side of the air filter and a second sensor input of the differential pressure sensor is fluidly coupled to the airway toward a patient-side of the air filter.

In a second implementation, the air filter is a first air filter, and wherein the second sensor input is fluidly coupled to the airway between the first air filter and a second air filter within the airway, wherein the second air filter is in the airway toward a patient-side of the second sensor input. In a third implementation, the air filter is positioned within the airway via a detachable coupling that is fluidly coupled between the manual ventilator and a patient-side opening.

In a fourth implementation, at least one of a cross-sectional area of the coupling is greater than a cross-sectional area of a flow line between the coupling and the patient-side opening, or a cross-sectional area of the air filter is greater than a cross-sectional area of the flow line of the airway.

In a fifth implementation, the air filter is configured to prevent at least 95% of airborne particles within the airway from entering a sensor line of the differential pressure sensor. In a sixth implementation, the manual ventilator is associated with a bag-valve-mask apparatus.

In a seventh implementation, the representation indicates at least one of whether a compression rate of the compression cycle is to be increased or decreased, whether a compression rate of a subsequent compression cycle is to be increased or decreased, or whether a time period between the compression cycle and a subsequent compression cycle is to be longer or shorter than a time period between the compression cycle and a previous compression cycle.

Although FIG. 3 shows example blocks of process 300, in some implementations, process 300 may include additional blocks, fewer blocks, different blocks, or differently arranged blocks than those depicted in FIG. 3. Additionally, or alternatively, two or more of the blocks of process 300 may be performed in parallel.

The foregoing disclosure provides illustration and description, but is not intended to be exhaustive or to limit the implementations to the precise form disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, etc., depending on the context.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   determining, by a differential pressure sensor of a device capable of being fit within a manual ventilator and via a first sensor line and a second sensor line, a differential pressure measurement associated with a differential pressure across an air filter, of a coupling of the device, positioned within a ventilator airway of the manual ventilator;
   receiving, by the device and from an absolute pressure sensor, of the device, via a third sensor line, an absolute pressure measurement associated with an absolute pressure of a patient airway near or toward a patient-side opening;
   determining, by the device and based on the differential pressure measurement and the absolute pressure measurement, an air flow rate through the ventilator airway;
   determining, by the device, a timing of a compression cycle of the manual ventilator;
   determining, by the device, a desired breathing cycle based on one or more characteristics of the device;
   determining, by the device and based on the timing, a flow threshold associated with the desired breathing cycle;
   determining, by the device, a difference between the flow threshold and the air flow rate; and
   providing, by the device and via a display associated with the manual ventilator, a representation associated with the difference to indicate whether a compression parameter of the compression cycle is to be adjusted.

2. The method of claim 1, wherein a first sensor input of the differential pressure sensor is fluidly coupled to the ventilator airway toward a manual ventilator-side of the air filter and a second sensor input of the differential pressure sensor is fluidly coupled to the ventilator airway toward a patient-side of the air filter.

3. The method of claim 2, wherein the air filter is a first air filter, and
   wherein the second sensor input is fluidly coupled to the ventilator airway between the first air filter and a second air filter within the ventilator airway,
   wherein the second air filter is in the ventilator airway toward the patient-side of the second sensor input.

4. The method of claim 2, wherein the air filter is positioned within the ventilator airway via the coupling, and wherein the coupling is fluidly coupled between the manual ventilator and the patient-side opening.

5. The method of claim 4, wherein at least one of:
   a cross-sectional area of the coupling is greater than a cross-sectional area of a flow line between the coupling and the patient-side opening; or
   a cross-sectional area of the air filter is greater than a cross-sectional area of the flow line of the ventilator airway.

6. The method of claim 1, wherein the air filter is configured to prevent at least 95% of airborne particles within the ventilator airway from entering at least one of the first sensor line or the second sensor line.

7. The method of claim 1, wherein the manual ventilator is associated with a bag-valve-mask apparatus.

8. The method of claim 1, wherein the representation indicates at least one of:
   whether a compression rate of the compression cycle is to be increased or decreased;
   whether a compression rate of a subsequent compression cycle is to be increased or decreased; or
   whether a time period between the compression cycle and a subsequent compression cycle is to be longer or shorter than a time period between the compression cycle and a previous compression cycle.

9. The method of claim 1, wherein the first sensor line and the second sensor line provide a first pressure measurement and a second pressure measurement, respectively,
   wherein the differential pressure measurement is based on the first pressure measurement and the second pressure measurement, and
   wherein the differential pressure measurement includes a polarity based on whether the first pressure measurement is greater than the second pressure measurement.

10. A device, comprising:
    an air filter, of a coupling of the device, configured to be positioned within an airway of a manual ventilator;
    a differential pressure sensor configured to provide a differential pressure measurement associated with a differential pressure across the air filter via a first sensor line and a second sensor line; and
    an absolute pressure sensor configured to measure an absolute pressure of a patient airway near or toward a patient-side opening via a third sensor line; and a monitor configured to:
  receive information indicating a differential pressure measurement and an absolute pressure measurement from the differential pressure sensor and the absolute pressure sensor, respectively;
  determine, based on the information indicating the differential pressure measurement and the absolute pressure measurement, an air flow rate through the airway;
  determine, based on the air flow rate and a flow threshold, whether a compression parameter of the manual ventilator requires adjustment,
    wherein the monitor, when determining whether the compression parameter requires adjustment, is configured to:
      determine a desired breathing cycle based on one or more characteristics of the device,
      determine a timing of a patient breathing cycle facilitated by the manual ventilator, and
      determine the flow threshold based on the timing and the desired breathing cycle; and
  provide, via a display associated with the manual ventilator, an indication associated with whether the compression parameter requires adjustment.

11. The device of claim 10, wherein the air filter is positioned within the coupling,
  wherein the coupling is located between the manual ventilator and the patient-side opening, and
  wherein a cross-sectional area of the coupling is greater than a cross-sectional area of a flow line of the airway.

12. The device of claim 11, wherein the monitor is further configured to:
  prior to determining the air flow rate, receive an input that identifies the cross-sectional area of the airway,
    wherein the air flow rate is determined based on the cross-sectional area of the airway.

13. The device of claim 10, wherein the monitor, when determining whether the compression parameter requires adjustment, is configured to:
  compare the air flow rate with the flow threshold,
    wherein the compression parameter requires adjustment based on whether a difference between the flow threshold and the air flow rate satisfies a difference threshold.

14. The device of claim 10, wherein the flow threshold is based on a timing of the desired breathing cycle that is to be facilitated by the manual ventilator.

15. The device of claim 10, wherein the manual ventilator is associated with a bag-valve-mask apparatus.

16. The device of claim 10, wherein the air filter is configured to filter at least 95% of airborne particles within the airway.

17. A manual ventilation system comprising:
  a manual ventilator including a ventilator airway and a patient-side opening,
    wherein the patient-side opening is configured to fluidly couple the ventilator airway with a patient airway;
  a manual ventilator assistant, separate from the manual ventilator and configured to assist a user in using the manual ventilator, including a coupling, a differential pressure sensor, an absolute pressure sensor, a first sensor line, a second sensor line, and a third sensor line,
    wherein the coupling includes an air filter and is configured to be fluidly coupled to the manual ventilator,
    wherein the differential pressure sensor is configured to measure a differential pressure across the air filter via the first sensor line and the second sensor line, and
    wherein the absolute pressure sensor is configured to measure an absolute pressure of the patient airway near or toward the patient-side opening via the third sensor line;
  a ventilation monitor configured to:
    receive information indicating a differential pressure measurement and an absolute pressure measurement from the differential pressure sensor and the absolute pressure sensor, respectively;
    determine, based on the information indicating the differential pressure measurement and the absolute pressure measurement, an air flow rate through the ventilator airway,
      determine a desired breathing cycle based on one or more characteristics of the manual ventilation system; and
    provide, via a display associated with the manual ventilator, an indication associated with the air flow rate and based on the desired breathing cycle.

18. The manual ventilation system of claim 17, wherein the air filter is a first air filter and the coupling includes a second air filter,
  wherein the first sensor line of the differential pressure sensor is fluidly coupled to the ventilator airway between the manual ventilator and the first air filter;
  wherein the second sensor line of the differential pressure sensor is fluidly coupled to the ventilator airway between the first air filter and the second air filter; and
  wherein the second air filter is positioned within the ventilator airway between the first air filter and the patient-side opening.

19. The manual ventilation system of claim 17, wherein the ventilation monitor is further configured to:
  prior to providing the indication, determine based on the air flow rate whether a compression parameter associated with a compression cycle of the manual ventilator requires adjustment; and
  generate the indication based on whether the compression parameter requires adjustment.

20. The manual ventilation system of claim 17, wherein the indication is configured to assist a user that is manually compressing the manual ventilator to facilitate breathing for a patient based on identifying at least one of:
  a compression rate of a compression cycle of the manual ventilator;
  whether the compression rate of the compression cycle is to be increased or decreased;
  whether a compression rate of a subsequent compression cycle is to be increased or decreased; or
  whether a time period between the compression cycle and a subsequent compression cycle is to be longer or shorter than a time period between the compression cycle and a previous compression cycle.

* * * * *